United States Patent [19]

Mortreux et al.

[11] Patent Number: 4,923,840
[45] Date of Patent: May 8, 1990

[54] ELECTROCHEMICAL CATALYTIC SYSTEM, THE PROCESS FOR PREPARATION THEREOF AND ITS APPLICATION TO THE PRODUCTION OF ALDEHYDES

[75] Inventors: André Mortreux, Hem; Francis Petit, Villeneuve D'Ascq; Sylvain Mutez, Tourcoing; Eric Paumard, Ronchin, all of France

[73] Assignee: Exxon Chemical COmpany, Abingdon, United Kingdom

[21] Appl. No.: 341,233

[22] Filed: Apr. 18, 1989

Related U.S. Application Data

[63] Continuation of Ser. No. 98,697, Sep. 18, 1987, abandoned, which is a continuation-in-part of Ser. No. 934,602, filed as PCT FR86/00081 on Mar. 12, 1986, published as WO86/05415 on Sept. 25, 1986, abandoned.

[30] Foreign Application Priority Data

Mar. 13, 1985 [FR] France .................................. 85 03670

[51] Int. Cl.$^5$ .............................................. B01J 31/22
[52] U.S. Cl. ................................ 502/167; 502/162; 204/59 R; 204/59 QM
[58] Field of Search ............. 502/162, 167; 204/59 R, 204/59 QM

[56] References Cited

U.S. PATENT DOCUMENTS

| | | | |
|---|---|---|---|
| 3,516,978 | 6/1970 | Mottus et al. | 526/110 |
| 3,546,083 | 12/1970 | Ort et al. | 204/131 |
| 3,677,911 | 7/1972 | Mottus et al. | 204/59 QM |
| 3,684,739 | 8/1972 | Mottus et al. | 502/117 |
| 3,700,710 | 10/1972 | Mottus et al. | 502/103 X |
| 3,773,632 | 11/1973 | Lehmkuhl | 204/59 QM |
| 3,981,925 | 9/1976 | Schwager et al. | 502/167 X |
| 4,358,621 | 11/1982 | Sakakibara et al. | 568/454 |
| 4,358,623 | 11/1982 | Murphy et al. | 568/473 |
| 4,370,258 | 1/1983 | Ogata et al. | 502/162 |
| 4,542,119 | 9/1985 | Hsu et al. | 502/162 X |

FOREIGN PATENT DOCUMENTS

| | | |
|---|---|---|
| 2550201 | 4/1983 | France . |
| 1182651 | 4/1967 | United Kingdom . |

OTHER PUBLICATIONS

Lapporte et al., J. Olg. Chem., 28 (Jul., 1963), pp. 1947–1948.
101 Chemical Abstracts (16) 139669X (Oct. 1964).
PCT Search Report No. WO86/05415 for PCT/FR86/00081.

*Primary Examiner*—Patrick P. Garvin
*Attorney, Agent, or Firm*—Finnegan, Henderson, Farabow, Garrett & Dunner

[57] ABSTRACT

The catalytic system comprises:

at least one platinum complex of formula $LPtX_2$ in which L is an organic compound containing at least two phosphorus atoms capable of coordinating platinum and X is a halogen atom, and at least organic tin compound comprising at least one Sn—O bond and at least one C—O bond.

Application to the production of aldehydes by the hydroformlation of an ethylenically unsaturated organic compound, by reacting the said organic compound, at a temperature of between 10° C. and 300° C. and under a pressure of between 1 and 350 bars, with a mixture of carbon monoxide and hydrogen in the presence of an effective amount of the said catalytic system.

19 Claims, No Drawings

ELECTROCHEMICAL CATALYTIC SYSTEM, THE PROCESS FOR PREPARATION THEREOF AND ITS APPLICATION TO THE PRODUCTION OF ALDEHYDES

This application is a continuation of application Ser. No. 098,697, filed Sept. 18, 1987, now abandoned, which is a continuation-in-part application of application Ser. No. 934,602, filed as PCT FR86/00081 on Mar. 12, 1986, published as WO86/05415 on Sep. 25, 1986 and now abandoned.

The present invention relates to a catalytic system, a process for the preparation thereof and its application to the production of aldehydes by the hydroformylation of ethylenically unsaturated organic compounds.

The objective of the present invention consists in obtaining, by the hydroformylation of olefins, a mixture of normal and branched aldehydes in which the proportion of normal aldehydes is as high as possible.

A first subject of the present invention consists of a catalytic system, characterized in that it comprises:
at least one platinum complex of formula $LPtX_2$ in which L is an organic compound containing at least two phosphorus atoms capable of coordinating platinum and X is a halogen atom, and
organic tin compound comprising at least one Sn—O bond and at least one C—O bond. The organic tin compound can include an alkene carbonate, which preferably has 2 to 6 carbon atoms.

In the catalytic system according to the present invention, the platinum complex and the organic tin compound comprising at least one Sn—O bond and at least one C—O bond are preferably present in respective proportions such that the atomic ratio Sn/Pt is between 0.2 and 5.

The catalytic system according to the invention comprises, as a first component, at least one platinum complex of formula $LPtX_2$ in which X can be chosen in any manner from fluorine, chlorine, bromine and iodine. The organic phosphorus compound L can be, for example:
a bis(diphenylphosphino)alkane of formula

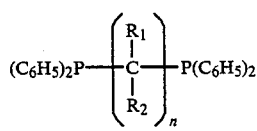

(I)

in which $R_1$ and $R_2$, which are identical or different are chosen from the hydrogen atom and aliphatic hydrocarbon radicals, the latter bearing functional groups if appropriate, and/or being linked to each other, and n is greater than or equal to 4;
an aminophosphine phosphinite of formula

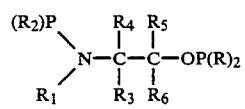

(II)

in which:
R is an aliphatic, alicyclic or aromatic hydrocarbon radical,
$R_1$ is chosen from the hyrogen atom and hydrocarbon radicals,
$R_3$ and $R_4$, which must differ from each other, are chosen from the hydrogen atom and hydrocarbon radicals which may, if appropriate, bear at least one functional group chosen from alcohol, thiol, thioether, amine, imine, acid, ester, amide and ether groups, and
$R_5$ and $R_6$ are chosen from the hydrogen atom and hydrocarbon radicals, bearing functional groups if appropriate.

(1S,2S)-(+)-trans-1,2-Bis(diphenylphosphinomethyl)cyclohexane, 1,4-bis(diphenylphosphino)butane and 2,3-isopropylidenedihydroxy-1,4-bis(diphenylphosphino)butane constitute examples of phosphorus organic compounds of formula (I) which can be used within the scope of the present invention. Furthermore, some compounds of formula (II) and the way in which they are prepared have been described in French Patent Application No. 2,550,201.

The catalytic system according to the invention comprises, in addition, at least one organic tin compound comprising at least one Sn—O bond and at least one C—O bond.

Such organic tin compound may be, for example, a combination formed between tin and an alkene carbonate, or a tin alcoholate or a tin cyclic alcoholate. Among combinations formed between tin and an alkene carbonate, combinations where the alkene group of the alkene carbonate has from 2 to 6 carbon atoms, such as propylene carbonate, ethylene carbonate, 1-2 butylene carbonate and 1-2 hexylene carbonate, are preferred. Examples of tin alcoholates which may be used according to the invention are compounds having the formula $(R_1O)Sn(OR_2)$ where $R_1$ and $R_2$, either identical or different, are both hydrocarbon groups having preferably from 1 to 12 carbon atoms, such as for example $Sn(OCH_3)_2$ and $Sn(OC_2H_5)_2$. Examples of tin cyclic alcoholates which may be used according to the invention are compounds having the formula:

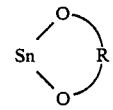

In this formula, R is a hydrocarbon group having from 2 to 12 carbons atoms, such as for example propylene stannate and o-phenylene stannate (o-phenylene dioxytin-II). The tin alcoholates may be prepared according to the method disclosed by J. Morrison and H. Haendler, 29 J. Inorg. Nucl. Chem. 393–400 (1967). Tin cyclic alcoholates may be prepared according to the method disclosed by J. Zuckerman, J. Chem. Soc. 1322 (1963). In this method, propylene stannate and orthophenylene stannate (orthophenylene dioxytin-II) are obtained from 1-2 propanediol and catechol respectively. Combinations formed between tin and an alkene carbonate may be formed, for example, by reduction.

The said organic tin compound can be formed by reduction of an electrochemical solvent containing at least one alkene carbonate in an electrochemical cell comprising a tin anode and a platinum cathode, by bringing the cathode to a potential less than or equal to $-0.2$ V and maintaining this potential constant for a sufficient time to provide for the production of an amount of electricity greater than or equal to 0.5 faraday per gram-atom of platinum. In this case, the electrochemical cell can comprise, in addition, a reference electrode chosen from known electrodes such as, in particular, Ag/AgCl, Ag/Ag+, Hg/Hg$_2$Cl$_2$ (calomel), the cathode potential then being calculated relative to the said reference electrode. According to an embodiment of the present invention, the reduction of the electrochemical solvent can be performed in the presence of a small amount of a conductive salt which is soluble in the electrochemical solvent, such as for example, tetra-n-butylammonium hexafluorophosphate. The presence of this conductive salt enables the reduction of the solvent to be advantageously accelerated, especially at a moderate temperature. The electrochemical reduction phase according to the invention is generally performed at a temperature of between 10° C. and 70° C., the electrochemical cell being maintained under an atmosphere of an inert gas such as nitrogen. The electrochemical solvent used in the context of the present invention necessarily comprises at least one alkene carbonate as defined above. The electrochemical solvent may comprise a further solvent miscible with the alkene carbonate, for example an aromatic hydrocarbon such as benzene, toluene or the like. In such case, the electrochemical solvent mixture may comprise up to 90% by volume of the further solvent. When the combination formed between tin and an alkene carbonate is produced electrochemically as described above, such a combination is insoluble in water and all organic solvents at room temperature as well as at elevated temperatures and its elementary analysis does not correspond to any known tin compound. It is assumed that such combination corresponds to a mixture of definite tin compounds. Infrared analysis may provide further information on the structure of such a combination. For example, where the alkene carbonate is propylene carbonate, the infrared spectrum shows signals at 3400 cm$^{-1}$ (O—H bond), 1620 cm$^{-1}$ (C=O bond), 1120-1045 cm$^{-1}$ (C—O bond) and 540 cm$^{-1}$ (Sn—O bond).

A second subject of the present invention consists of a process for the preparation of a catalytic system as described above. Such a process consists in reacting at least one organic tin compound comprising at least one organic tin compound comprising at least one Sn—O bond and at least one C—O bond with at least one platinum complex of formula LPtX$_2$ in at least one solvent for the said complex, at a temperature of between 10° C. and the boiling point of the said solvent. Among solvents for the platinum complex of formula LPtX$_2$, aromatic hydrocarbons (such as, for example, benzene, toluene and xylenes) and alkene carboates, in particular those in which the alkene group has from 2 to 6 carbon atoms, may be mentioned in particular. For carrying out the process according to the invention, it is preferable to use a solvent comprising at least 25% by volume of alkene carbonate. The time for the reaction between the combination based on tin and the platinum complex can vary, according to the usual rules well known to those skilled in the art, depending on the reaction temperature chosen and the concentration of the reactive species in the solvent. By way of example, this time is generally not longer than 20 minutes when the reaction temperature is equal to 80° C.

Several embodiments can be envisaged in the context of the process according to the present invention. A first embodiment consists in forming a complex combination of tin and an alkene carbonate, for example by an an electrochemical method as described above, and then introducing the platinum complex into the medium in which the complex combination of tin has been formed, the said medium already comprising the solvent required for the reaction. A second embodiment consists in forming a complex combination of tin and an alkene carbonate, for example by an electrochemical method as described above, in isolating in powder form the said complex combination from the medium in which it has been formed (for example by filtering, washing and drying the precipitate which is formed in the electrochemical cell), and then in introducing the said powder into a solution of the platinum complex in the solvent required for the reaction. Finally, a third embodiment consists in forming the complex combination of tin and an alkene carbonate in the presence of the solvent and the platinum complex, for example by an electrochemical method as described above.

Regardless of the embodiment chosen for the process according to the invention, it is desirable that the concentration of the platinum complex in the reaction solvent should be between 0.01 and 0.2 mole per liter.

A third subject of the present invention consists of the application of the catalytic system described above to the production of aldehydes by the hydroformylation of an ethylenically unsaturated organic compound, characterized in that the said organic compound is reacted, at a temperature of between 10° C. and 300° C. and under a pressure of between 1 to 350 bars, with a mixture of carbon monoxide and hydrogen in the presence of an effective amount of the said catalytic system. An effective amount of the catalytic system is generally such that the mole ratio of the ethylenically unsaturated organic compound to platinum is between 100 and 10,000.

The mole ratio CO$_{/H_2}$ in the mixture of carbon monoxide and hydrogen involved in the hydroformylation reaction according to the invention is generally between 0.5 and 2.

Among ethylenically unsaturated organic compounds which can be subjected to the hydroformylation reaction according to the invention, the following may be mentioned in particular:
olefins having from 2 to 12 carbon atoms, such as, in particular, propylene, 1-butene, 1-hexene, 1-octene, and the like;
aromatic vinyl compounds such as styrene;
dienes such as, for example, 4-vinylcyclohexane.

The time for the hydroformylation reaction according to the invention is generally between 0.5 and 100 hours.

The examples below are given by way of illustration and without implied limitations of the present invention.

EXAMPLES 1 TO 4

Preparation of catalytic systems 60 mg of complex LPtCl$_2$, the ligand L being 2,3-isopropylidenedihydroxy-1,4-bis(diphenylphosphino)butane, are introduced under nitrogen into a glass electrochemical cell, followed by the solvent consisting of 25 cm$^3$ of a mixture of benzene and alkene carbonate. After complete dissolution of the catalyst, the cathode (consisting of a platinum basket) and the anode (consisting of a cylinder of tin) are immersed in the solvent, followed by the reference electrode (Ag/AgCl/N(C$_2$H$_5$)$_4$Cl 0.1M in the alkene carbonate). With the temperature equal to 20° C., the reduction potential is set at −1.85 V and the quantity of current flowing in the circuit is measured using a coulometer. The amount of tin required for the reaction is measured by weighing the anode before and after the reduction (the mass obtained by weighing is generally identical to that determined from the quantity of coulombs flowing in the circuit). Under these conditions, the atomic ratio Sn/Pt is equal to 2.5.

In Examples 1 to 3, the solvent comprises 15 cm$^3$ of benzene, the alkene carbonate being, respectively: propylene carbonate for Example 1, ethylene carbonate for Example 2, and 1,2-hexylene carbonate for Example 3.

In Example 4, the solvent comprises 2 cm$^3$ of benzene and 23 cm$^3$ of propylene carbonate.

EXAMPLES 5 TO 8

Hydroformylation reaction

A catalytic system prepared in accordance with one of Examples 1 to 4 is introduced into a 100-cm$^3$ stainless steel autoclave reactor equipped with a bar magnet stirring system, and 1.23 gram of styrene is then added. The reactor is heated to a temperature of 80° C. and then charged with the synthesis gas, consisting of an equimolar mixture of carbon monoxide and hydrogen. Finally, the mixture is stirred and the reaction is continued at 80° C. under a pressure of 50 bars for 24 hours. A mixture comprising ethylbenzene, 2-phenylpropanal and 3-phenylpropanal is then obtained, with a degree of conversion DC (expressed as a percentage). Analysis of this mixture permits the determination, on the one hand of the proportion by weight of ethylbenzene EB (expressed as a percentage), and on the other hand of the mole ratio n/b of the normal aldehyde to the branched aldehyde. Table I below summarizes the results obtained in relation to the catalytic system used.

TABLE I

| Example | Catalyt. system | DC | EB | n/b |
| --- | --- | --- | --- | --- |
| 5 | Ex. 1 | 40 | 2.5 | 6.25 |
| 6 | Ex. 2 | 45 | 5 | 3.7 |
| 7 | Ex. 3 | 38 | 12 | 2.3 |
| 8 | Ex. 4 | 17 | 0.2 | 8.3 |

EXAMPLE 9

The solvent consisting of a mixture of 15 cm$^3$ of benzene and 10 cm$^3$ of propylene carbonate is introduced into the electrochemical cell described in Example 1, and the electrochemical reduction of the said solvent is then performed under conditions identical to those of Example 1. 60 mg of complex LPtCl$_2$, the ligand L being 1,4-bis(diphenylphosphino)butane, are then added.

EXAMPLE 10

The catalytic system prepared in accordance with Example 9 is used to perform the hydroformylation reaction of 3.57 grams of 1-hexene in an autoclave reactor identical to that of Example 5, by means of an equimolar mixture of hydrogen and carbon monoxide. The pressure P (expressed in bars), the temperature T (expressed in degrees Celsius) and the time t (expressed in hours) for the reaction are shown in Table II. A mixture of hexane, 2-hexane, 2-methylhexanal and n-heptanal is then obtained, with a degree of conversion DC (expressed as a percentage). Analysis of the aldehydes formed enables the mole ratio n/b of the normal aldehyde to the branched aldehyde to be determined. Table II below summarizes the results obtained.

EXAMPLES 11 TO 13

The electrochemical reduction of the solvent is performed under conditions identical to those of Example 9, with the exception of the reduction potential, in this case equal to −60 V. 60 mg of complex LPtCl$_2$ are then added, the ligand L being:

(1S,2S)-(+)-trans-1,2-bis(diphenylphosphinomethyl)-cyclohexane for Example 11;

2,3-isopropylidenedihydroxy-1,4-bis(diphenylphosphino)butane for Example 12;

1,4-bis(diphenylphosphino)butane for Example 13.

EXAMPLES 14 AND 15

The catalytic systems prepared in accordance with Examples 11 and 12 are used to perform hydroformylation of 1-hexane under the conditions of Example 10. Table II below summarizes the results obtained.

TABLE II

| Example | Catalyt. system | T | t | DC | EB | n/b |
| --- | --- | --- | --- | --- | --- | --- |
| 10 | Ex. 9 | 50 | 80 | 24 | 83 | 56 |
| 14 | Ex. 11 | 100 | 90 | 6 | 100 | 28 |
| 15 | Ex. 12 | 100 | 90 | 6 | 98 | 32 |

EXAMPLES 16 TO 18

The catalytic systems prepared in accordance with Examples 11 to 13 are used to perform hydroformylation of styrene, under the conditions of Example 5 apart from the following exceptions:

amount of styrene introduced into the reactor: 0.25 gram;

reaction pressure: 100 bars.

The temperature T (expressed in degrees Celsius) and the time t (expressed in hours) for the reaction are shown in Table III below, as well as the results obtained, expressed as in Examples 5 to 8 above.

TABLE III

| Example | Catalyt. system | T | t | DC | EB | n/b |
| --- | --- | --- | --- | --- | --- | --- |
| 16 | 11 | 90 | 4 | 100 | 7 | 3.8 |
| 17 | 12 | 100 | 24 | 67 | 8 | 3.0 |
| 18 | 13 | 100 | 24 | 25 | 4 | 3.0 |

EXAMPLES 19 AND 20

A solvent consisting of a mixture of 15 cm$^3$ of benzene and 10 cm$^3$ of propylene carbonate is introduced under nitrogen into a glass electrochemical cell. The cathode (consisting of a platinum basket) and the anode (consisting of a cylinder of tin) are immersed in this solvent. With the temperature equal to 20° C., the reduction potential is set at −60 V. The gradual formation of a precipitate is observed, and this is isolated by filtration and purified by washing. The powder thereby obtained is subjected to elementary analysis by weight, which gives the following results:

| | |
| --- | --- |
| C | 14.0% |
| H | 1.8% |
| O | 20.6% |
| Sn | 63.6% |

After the reactor described in Example 5 has been outgassed, the complex LPtCl$_2$ is introduced into this reactor while the latter is scavenged with nitrogen, the ligand L in the complex being:

(1S,2S)-(+)-trans-1,2-bis(diphenylphosphinomethyl)-cyclohexane for Example 19;
2,3-isopropylidenedihydroxy-1,4-bis(diphenylphosphino)butane for Example 20.

The powder obtained above is then introduced with stirring into this same reactor, in an amount such that the atomic ratio Sn/Pt is equal to 1, followed by styrene in an amount such that the mole ratio of styrene to platinum is equal to 100. The autoclave is then heated to a temperature of 90° C. after being charged with the synthesis gas, consisting of an equimolar mixture of carbon monoxide and hydrogen, at a pressure of 100 bars. The mixture is then stirred. After the reaction time t (expressed in hours) specified in Table IV below, the reactor is cooled and the gaseous mixture then removed. The recovered liquid phase is analyzed by gas chromatography, and the results obtained, expressed as in Examples 5 to 8 above, are shown in Table IV.

TABLE IV

| Example | t | DC | EB | n/b |
|---|---|---|---|---|
| 19 | 4 | 100 | 6 | 4.9 |
| 20 | 2.5 | 99 | 10 | 2.9 |

EXAMPLE 21

Tin methylate Sn(OCH$_3$)$_2$ is produced according to the method disclosed by J. Morrison and H. Haendler, 29 *J. Inorg. Nucl. Chem.*, 393–400 (1967). A catalytic system comprising 66.4 mg of LPtCl$_2$ (L being the same ligand as in example 12) and 15.7 mg tin methylate in a solvent consisting of a mixture of 15 cm$^3$ benzene and 10 cm$^3$ propylene carbonate is introduced under nitrogen into a 100 cm$^3$ stainless steel autoclave reactor equipped with a bar magnet stirring system. Then, 1.23 g styrene is added. The reactor is heated to a temperature of 90° C. and then filled with an equimolar mixture of carbon monoxide and hydrogen (synthesis gas). The resulting mixture is stirred and the reaction continued at 90° C. under a pressure of 100 bars for a time (T) expressed in hours. A mixture of ethylbenzene, 2-phenylpropanol and 3-phenylpropanol is obtained with a degree of conversion (DC). The proportion by weight of ethylbenzene (EB) and the molar ratio (n/b) are determined as above. The results are reported in Table V below.

EXAMPLE 22

The experimental conditions of example 21 are repeated except that 15.7 mg tin methylate are replaced by 18.1 mg tin ethylate produced according to the same method. The results are reported in Table V below.

EXAMPLE 23

The experimental conditions of example 21 are repeated except that 15.7 mg tin methylate are replaced by 19.7 mg o-phenylene stannate produced according to the method described by J. Zuckermann, *J. Chem. Soc.* 1322 (1963). The results are reported in Table V below.

TABLE V

| Example | T | DC | EB | n/b |
|---|---|---|---|---|
| 21 | 4 | 100 | 9 | 3.0 |
| 22 | 4 | 100 | 8 | 2.9 |
| 23 | 3 | 100 | 9.5 | 3.0 |

EXAMPLES 24 AND 25

Hydroformylation of 1-hexane is performed under conditions identical (pressure 100 bars, temperature 90° C.) to those of example 21 and using a catalytic system comprising LPtCl$_2$ (L being the same ligand as in example 12) and tin ethylate (example 24) or o-phenylene stannate (example 25) in such amounts that the atomic ratio Sn/Pt is 2.5. 1-hexene is present in such an amount that the molar ratio of 1-hexene to platinum is 500. The results are reported in Table VI below.

TABLE VI

| Example | T | DC | n/b |
|---|---|---|---|
| 24 | 24 | 100 | 21 |
| 25 | 5 | 100 | 13 |

We claim:

1. A catalytic system for the production of aldehydes by the hydroformylation of olefinically unsaturated compounds comprising:
   (a) at least one platinum complex of formula LPtX$_2$ in which L is an organic compound containing at least two phosphorus atoms capable of coordinating platinum and X is a halogen atom, and
   (b) at least one organic tin compound comprising at least one Sn—O bond and at least one C—O bond wherein said tin compound is selected from the group consisting of a tin compound mixed with an alkene carbonate, tin alcoholate, and tin cyclic alcoholates.

2. The catalytic system according to claim 1, wherein L is a bis(diphenylphosphino)alkene of formula I:

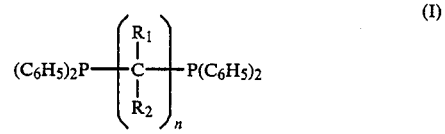

in which formula I R$_1$ and R$_2$, which may be identical or different, are chosen from a hydrogen atom and aliphatic hydrocarbon radicals, and n is greater than or equal to 4.

3. The catalytic system according to claim 1, wherein L is an aminophosphine phosphinite of formula II:

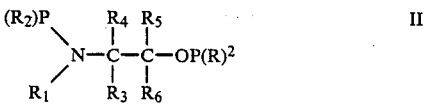

in which formula II:
   (i) R is an aliphatic, cycloaliphatic or aromatic hydrocarbon radical,
   (ii) R$_1$ is chosen from a hydrogen atom and hydrocarbon radicals,
   (iii) R$_3$ and R$_4$, which must differ from each other, are chosen from a hydrogen atom, hydrocarbon radicals, and substituted hydrocarbon radicals, and
   (iv) R$_5$ and R$_6$ are chosen from a hydrogen atom and hydrocarbon radicals.

4. The catalytic system according to claim 1, wherein the platinum complex and the organic tin compound are present in respective proportions such that the atomic ratio Sn/Pt is between 0.2 and 5.

5. A process for preparing a catalytic system comprising:
   (a) at least one platinum complex of formula $LPtX_2$ in which L is an organic compound containing at least two phosphorus atoms capable of coordinating platinum and X is a halogen atom, and
   (b) at least one organic tin compound comprising at least one Sn—O bond and at least one C—O bond wherein said organic tin compound is selected from the group consisting of a tin compound mixed with an alkene carbonate, tin alcoholate, and tin cyclic alcoholates, wherein in said process at least one said organic tin compound is reacted with at least one platinum complex of formula $LPtX_2$ in at least one solvent for the organic tin compound at a temperature of between 10° C. and the boiling point of the solvent.

6. The preparation process according to claim 5, wherein the organic tin compound is formed by reduction of an elecrochemical solvent containing at least one alkene carbonate in an electrochemical cell comprising a tin anode and a platinum cathode, by bringing the cathode to a potential less than or equal to $-0.2$ V and maintaining this potential constant for a sufficient time to provide for the production of an amount of electricity greater than or equal to 0.5 faraday per gram-atom of platinum.

7. The process according to claim 6, wherein the reduction of the electrochemical solvent is performed in the presence of a small amount of a conductive salt which is soluble in the solvent.

8. The process according to claim 6 wherein the reduction of the electrochemical solvent is performed at a temperature of between 10° C. and 70° C., the electrochemical cell being maintained under an inert gas atmosphere.

9. The process according to claim 6 wherein the electrochemical solvent further comprises an aromatic hydrocarbon mixed with the alkene carbonate.

10. The process according to claim 5, wherein the solvent for the platinum complex is chosen from aromatic hydrocarbons and alkene carbonates.

11. The process according to claim 10, wherein said solvent comprises at least 25% by volume of an alkene carbonate.

12. The process according to claim 5 wherein the concentration of the platinum complex in the reaction solvent is between 0.01 and 0.2 mole per liter.

13. The catalytic system according to claim 1, wherein the organic tin compound is present in a mixture with an alkene carbonate.

14. The catalytic system according to claim 13, wherein the alkene carbonate has 2 to 6 carbon atoms.

15. The catalytic system according to claim 3, wherein the hydrocarbon for $R_3$ and $R_4$ includes at least one substituent selected from the group consisting of alcohol, thio, thioether, amine, imine, acid, ester, amide, and ether.

16. The catalytic system according to claim 1, wherein the organic tin compound is selected from the group consisting of tin alcoholates and tin cyclic alcoholates.

17. The catalytic system according to claim 13, wherein the organic tin compound is selected from the group consisting of tin alcoholates and tin cyclic alcoholates.

18. The catalytic system according to claim 17, wherein the alkene carbonate is selected from the group consisting of propylene carbonate, ethylene carbonate, 1,2-butylene carbonate, and 1,2-hexylene carbonate.

19. The catalytic system according to claim 17, wherein
the tin alcoholate is of the formula $(R_1O)Sn(OR_2)$ wherein $R_1$ and $R_2$, either identical or different, are hydrocarbon radicals having 1 to 12 carbon atoms; and
the cyclic alcoholate is of the formula:

wherein R is a hydrocarbon radical having from 2 to 12 carbon atoms.

* * * * *